(12) United States Patent
Hattori et al.

(10) Patent No.: US 6,183,759 B1
(45) Date of Patent: Feb. 6, 2001

(54) COSMETIC COMPOSITION

(75) Inventors: Nobuaki Hattori; Masakazu Okumura, both of Takasago; Masato Yoshioka; Sueko Kobayashi, both of Osaka, all of (JP)

(73) Assignees: Nippon Fine Chemical Co., Ltd.; Seiwa Kasei Co., Ltd., both of Osaka (JP)

( * ) Notice: Under 35 U.S.C. 154(b), the term of this patent shall be extended for 0 days.

(21) Appl. No.: 09/066,577

(22) Filed: Apr. 27, 1998

(30) Foreign Application Priority Data

Apr. 28, 1997 (JP) .................................................. 9-111096

(51) Int. Cl.⁷ ................................ A61K 6/00; A61K 7/00; A61K 7/06; A61K 7/11
(52) U.S. Cl. .................. 424/401; 424/70.11; 424/70.14; 514/887
(58) Field of Search .................. 424/401, 70.14, 424/70.11; 514/887

(56) References Cited

U.S. PATENT DOCUMENTS

| | | | |
|---|---|---|---|
| 4,749,515 | 6/1988 | Miyamoto et al. | 252/545 |
| 5,556,970 | 9/1996 | Kawasaki et al. | 554/190 |
| 5,747,015 | * 5/1998 | Oshika et al. | 424/70.14 |

FOREIGN PATENT DOCUMENTS

| | | |
|---|---|---|
| 63-105000 | 5/1988 | (JP) . |
| 460086B2 | 9/1992 | (JP) . |
| 6122610 | 5/1994 | (JP) . |
| 6128193 | 5/1994 | (JP) . |
| 6293614 | 10/1994 | (JP) . |

\* cited by examiner

Primary Examiner—Theodore J. Criares
(74) Attorney, Agent, or Firm—Birch, Stewart, Kolasch & Birch, LLP

(57) ABSTRACT

An acylated peptide or a salt thereof obtainable by condensing a protein-derived peptide with a lanolin-derived non-hydroxyl fatty acid containing 30–45% by weight of iso-type fatty acid of the following formula (I), 30–50% by weight of anteiso-type fatty acid of the following formula (II), 10–30% by weight of normal type fatty acid of the following formula (III):

$$CH_3-CH(CH_3)-(CH_2)_n-COOH \quad (n=6\sim27) \quad (I)$$

$$CH_3CH_2-CH(CH_3)-(CH_2)_n-COOH \quad (n=6\sim26) \quad (II)$$

$$CH_3-(CH_2)_n-COOH \quad (n=8\sim28) \quad (III)$$

and less than 10% by weight of hydroxyl fatty acid, the total amount of said iso-type fatty acid and said anteiso-type fatty acid being at least 60% by weight; and a cosmetic composition for hair or skin containing the acylated peptide or a salt thereof; and the cosmetic composition gives excellent moist feel and gloss and the like to hair and an excellent feeling on use, such as smoothness and moistness to skin.

17 Claims, No Drawings

COSMETIC COMPOSITION

TECHNICAL FIELD OF THE INVENTION

The present invention relates to a cosmetic composition and acylated peptides suitable for incorporating in said cosmetic composition.

PRIOR ART

In recent years, there has been a progressive increase in the damage to hair, such damage includes an increase in the hydrophilic nature of the surface of hair, the damage by hair cuticles on the surface and even structural change in the cortex of the hair, damage due to various chemical treatment and beauty treatment, including permanent wave, hair-dyeing and so on, and also damage due to the effect of ultraviolet rays and waste gases. Such damage to hair may cause split hair, broken hair, poor gloss and color, poor feel to the touch and the like. As a measure for preventing such damage to hair or recovering the original nature of damaged hair, there have been proposed various cosmetic compositions for hair, including shampoo, hair rinse, hair treatment and the like, which contain acylated peptides imparted with an ability of surface-activation and an ability of decreasing friction on the surface of hair by acylating, with a higher fatty acid, a hydrolysate of a protein which is known to have an ability to retain moisture. For example, the patent publication JP-A-63-105000 discloses various cosmetic compositions for hair containing an acylated peptide which is obtained by the acylation of a casein-derived peptide with an acyl group having 8–20 carbon atoms. The patent publication JP-B-4-60086 discloses a shampoo containing an acylated peptide obtained by acylating a peptide having an average molecular weight of 200–1,000 with a fatty acid halide having 8–22 carbon atoms.

It is also proposed to incorporate these acylated peptides into cosmetic composition for skin in order to give protection of and retention of moisture in the skin.

Satisfactory effects for the prevention of damage to hair and recovery from damaged hair, however, has not been obtained by incorporating these known acylated peptides into a cosmetic composition for hair. Particularly unsatisfactory are the effects on the feel of the hair, the feeling during use or the like.

In addition, unsatisfactory is the feel to the touch, the feeling during use or the like has been shown for cosmetic compositions of the poor art for skin.

As a result of extensive studies for solving the problems of the known cosmetic composition for hair and cosmetic composition for skin, the present inventors have found that satisfactory effect for the prevention of damage to hair and the recovery from damaged hair, and further, a drastic improvement in feel to the touch, moist feel, gloss and the like can be obtained by incorporating, in a cosmetic composition for hair, an acylated peptide or a salt thereof which is obtainable by condensing a protein-derived peptide produced by hydrolysis of a protein, with a specific lanolin fatty acid.

The present inventors have further found the fact that a cosmetic composition containing such acylated peptide or a salt thereof has sufficient ability to protect and retain skin and excellent feeling upon use. Thus, the present invention has been completed.

DISCLOSURE OF THE INVENTION

The present invention provides an acylated peptide or a salt thereof which is obtainable by condensing a protein-derived peptide produced by hydrolysis of a protein, with a lanolin-derived non-hydroxyl fatty acid containing 30–45% by weight of iso-type fatty acid of the following formula (I), 30–50% by weight of anteiso-type fatty acid of the following formula (II), 10–30% by weight of normal type fatty acid of the following formula (III):

*iso-type fatty acid

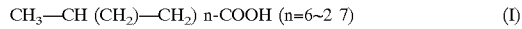
$$CH_3—CH\ (CH_2)—CH_2)\ n\text{-}COOH\ (n=6\sim27) \quad (I)$$

*anteiso-type fatty acid

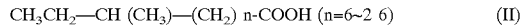
$$CH_3CH_2—CH\ (CH_3)—(CH_2)\ n\text{-}COOH\ (n=6\sim26) \quad (II)$$

*normal type fatty acid

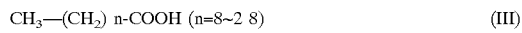
$$CH_3—(CH_2)\ n\text{-}COOH\ (n=8\sim28) \quad (III)$$

and less than 10% by weight of hydroxyl fatty acids, the total amount of said iso-type fatty acid and said anteiso-type fatty acid being at least 60% by weight.

The term "hydroxyl fatty acid" means a fatty acid having one or more hydroxyl groups in the molecule. Examples of the hydroxyl fatty acid include the following fatty acid having a hydroxyl group at its α-position or ω-position:

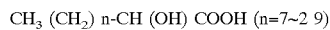
$$CH_3\ (CH_2)\ n\text{-}CH\ (OH)\ COOH\ (n=7\sim29)$$

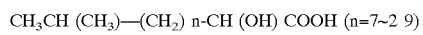
$$CH_3CH\ (CH_3)—(CH_2)\ n\text{-}CH\ (OH)\ COOH\ (n=7\sim29)$$

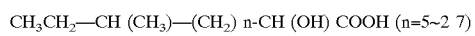
$$CH_3CH_2—CH\ (CH_3)—(CH_2)\ n\text{-}CH\ (OH)\ COOH\ (n=5\sim27)$$

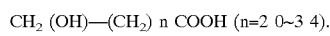
$$CH_2\ (OH)—(CH_2)\ n\ COOH\ (n=20\sim34).$$

The present invention further provides a cosmetic composition, for example, a cosmetic composition for hair, a cosmetic composition for skin or the like, containing an acylated peptide or a salt thereof which is obtainable by condensing a protein-derived peptide produced by hydrolysis of a protein, with a lanolin-derived non-hydroxyl fatty acid containing 30–45% by weight of iso-type fatty acid of formula (I), 30–50% by weight of anteiso-type fatty acid of formula (II), 10–30% by weight of normal type fatty acid of formula (III) and less than 10% by weight of hydroxyl fatty acids, the total amount of said iso-type fatty acid and said anteiso-type fatty acid being at least 60% by weight. (Hereinafter, said lanolin-derived non-hydroxyl fatty acid is referred to as "non-hydroxyl lanolin fatty acid".)

The average number of carbon atoms of the iso-type fatty acid of formula (I), the anteiso-type fatty acid of formula (II) and the normal type fatty acid of formula (III) in the non-hydroxyl lanolin fatty acid used in the present invention are preferably 15 to 24 and more preferably 17 to 22. The content of branched fatty acids, that is, iso-type fatty acid and anteiso-type fatty acid, having 20 or more carbon atoms is preferably less than 40% by weight.

Further, the content of the iso-type fatty acid of formula (I), the anteiso-type fatty acid of formula (II) and the normal type fatty acid of formula (III) in the non-hydroxyl lanolin fatty acid used in the present invention are preferably 30–35% by weight, 35–45% by weight and 12–16% by weight, respectively.

The non-hydroxyl lanolin fatty acid used in the present invention can be produced by a process described in the patent publication JP-A-6-293614. That is, they can be obtained by converting a known lanolin fatty acid or a lower alcohol ester thereof to a orate thereof which is then distilled to separate the non-hydroxyl lanolin fatty acid or a lower alcohol ester thereof from the borate of a hydroxyl lanolin fatty acid or a lower alcohol ester thereof. Hoverer, the process for the production thereof is not limited and may be any process that can give a fatty acid having the above-described composition.

The protein-derived peptide used in the present invention can be obtained by hydrolyzing a protein with an acid, an alkali or a proteolytic enzyme. The molecular weight of the protein-derived peptide is usually 100–30,000 and preferably 200–5,000. (Molecular weight of protein-derived peptide in this specification means number average molecular weight unless otherwise indicated.) It is possible to adjust the molecular weight of the protein-derived peptide by appropriately selecting the amount of an acid, an alkali or a proteolytic enzyme, the reaction temperature or the reaction time. The production of the protein-derived peptide used in the present invention can be carried out by a process and under conditions similar to those described in the patent publication JP-A-63-105000, JP-B-4-60086 and others.

The protein used for the production of the peptide is preferably a natural protein. Among natural proteins, collagen, keratin, silk protein, casein, soybean protein and wheat protein are particularly preferred. Soybean protein is a protein obtained from soybean and the like, which can be obtained, for example, by extracting defatted soybean seed with water, followed by precipitation at isoelectric point at pH 4–5. Wheat protein is a protein obtained from wheat and the like, which can be obtained, for example, by extracting defatted wheat seed with water, followed by precipitation at isoelectric point. Silk protein is a protein obtained from a cocoon, a silk thread, a silk cloth, and the like.

Various peptides commercially available can also be used as the protein-derived peptide used in the present invention. Examples of the peptides commercially available include collagen-derived peptide (Crotein A, manufactured by Croda Japan Co., Ltd.), keratin-derived peptide (Promois WK-HP, manufactured by Seiwa Kasei Co., Ltd.), silk protein-derived peptide (Promois Silk-700SP, manufactured by Seiwa Kasei Co., Ltd.), casein-derived peptide (Promois Milk-P, manufactured by Seiwa Kasei Co., Ltd.), soybean protein-derived peptide (Hydrosoy 2000SF, manufactured by Croda Japan Col., Ltd.) and wheat protein-derived peptide (Hydrotriticum 2000, manufactured by Croda Japan Co., Ltd.).

The condensation of the non-hydroxyl lanolin fatty acid with the protein-derived peptide can be carried out according to the following manner. That is, a protein-derived peptide is most generally acylated according to Schotten-Baumann reaction with a non-hydroxyl lanolin fatty acid halide in an aqueous solution under an alkaline condition at pH 7–14, preferably at pH 8–10, to give an acylated peptide. In this reaction, pH is maintained by adding an alkali, such as sodium hydroxide or potassium hydroxide, little by little in order to avoid the lowering of pH during the progress of the reaction. The reaction is carried out at a temperature of 0–60° C., preferably of 20–40° C., for 1–6 hours. Acid halide is most generally acid chloride but may be another acid halide such as acid bromide or acid iodide.

Other methods than the above-described Schotten-Baumann reaction can also be adopted, such as a method in which anon-hydroxyl lanolin fatty acid or a lower alcohol ester thereof is subjected to dehydration-condensation or dealcoholization-condensation with a protein-derived peptide at an elevated temperature of 150–200° C. under an elevated pressure. Alternatively, a method can be adopted in which a protein-derived peptide is reduced to give a product having a thiol group and then said product is heated together with a non-hydroxyl lanolin fatty acid in the presence or absence of an acid or an alkaline catalyst to give an ester.

The acylated peptide obtained in this manner can be incorporated as it is into a cosmetic composition after neutralization. Preferably, the acylated peptide is used after purification in which it is added to a strongly acidic solution such as hydrochloric acid, sulfuric acid or the like, to precipitate it and, then, the precipitated product is collected and washed with water. The acylated peptide thus obtained may be used either in the free form or may be converted into a salt form by neutralization. The acylated peptide may be used in the form of a solution in water, alcohol or a polyhydric alcohol such as propyleneglycol and the like or in the form of a dried powder. The concentration of the solution is preferably 10 to 60% by weight and more preferably 20 to 40%. Preferred alkali used for neutralization includes caustic alkali such as sodium hydroxide, potassium hydroxide and the like, ammonia, or an organic alkanolamine such as monethanolamine, diethanolamine, triethanolamine, 2-amino-2-methyl-1,3-propanediol and the like.

The cosmetic composition of the present invention include a cosmetic composition for hair, a cosmetic composition for skin, a foundation, a lip-stick, a soap, a cosmetic composition for nail and the like. Preferably, the acylated peptide or a salt thereof is used for a cosmetic composition for hair and a cosmetic composition for skin.

The cosmetic composition for hair according to the present invention includes all cosmetic compositions to be applied to hair. Examples thereof include cosmetic compositions for hair washing such as shampoo, hair rinse, hair conditioner, hair pack and the like, cosmetic compositions for hairdressing such as hair cream, hair tonic, hair spray and the like, agents possibly giving damage to hair by any chemical treatments such as permanent wave lotion, hair-dye, hair color rinse, bleaching agent, hair color manicure and the like and hair arrangement compositions such as mousse, gel and the like used on treatment with hot blast of drier.

The cosmetic composition for skin according to the present invention includes a face-washing composition, a toilet lotion, a cosmetic cream, a milky lotion and the like.

The cosmetic composition of the present invention may be in the form of various formulation such as an aqueous solution, an ethanolic solution, emulsion, suspension, gel, liquid crystal, solid, aerosol, etc. depending on use.

The amount of the acylated peptide or a salt thereof according to the present invention to be compounded in the cosmetic composition for hair is preferably about 0.01–20% by weight for nonaqueous oil-type compositions, about 0.01–30% by weight for nonaqueous cream-type compositions, about 0.1–30% by weight for shampoos, about 0.1–20% by weight for hair rinses, about 0.01–20% by weight and more preferably about 0.1$% by weight for the first agents of permanent wave, about 0.1–20% by weight and more preferably about 0.1–10% by weight for hair-dyes, about 0.05–10% by weight for hair color manicures, about 0.05– 10% by weight for bleaching agents, and about 0.05–10% by weight for hair arrangement compositions such as mousse, gel and the like.

The amount to be compounded in the cosmetic composition for skin, such as skin creams, milky lotions and the like, is preferably about 0.05–10% by weight.

The cosmetic composition of the present invention may contain known ingredients for cosmetic compositions in addition to the acylated peptide or a salt thereof according to the present invention. For example, the cosmetic composition of the present invention may contain optional ingredients described in the patent publication JP-B-6-39592 and JP-A-8-310920.

EXAMPLES

The present invention will now be described in more detail based on Examples, which should not be construed as a limitation upon the scope of the present invention.

Example 1

Synthesis of a potassium salt of a condensate of non-hydroxyl lanolin fatty acid and collagen-derived peptide At 55° C. was molten 312 g (1 mol) of a non-hydroxyl lanolin fatty acid (having an acid value of 180; containing 34.4% by weight of the iso-type fatty acid of formula (I), 39.2% by weight of the anteiso-type fatty acid of formula (II), 24% by weight of the normal type fatty acid of formula (III), and 2.4% by weight of hydroxyl fatty acids; the average carbon number of said iso-type fatty acid, anteiso-type fatty acid and normal type fatty acid being 19.3; and the total content of said iso-type fatty acid and said anteiso-type fatty acid having 20–32 carbon atoms being 38.6% by weight). To this was added dropwise 69 g (0.5 mol) of phosphorus trichloride over about 30 minutes. The mixture was stirred at 55–60° C. for 3 hours and allowed to stand for 8 hours. Then the lower layer containing of phosphorous acid was removed to give a crude acid chloride. The crude acid chloride was distilled in a glass distillation apparatus to give 324 g of an acid chloride.

Into a solution obtained by dissolving 150 g of a collagen-derived peptide (CCP-100P manufactured by Nikko Chemicals Co., Ltd., having an average molecular weight of 1,000) in 350 g water was added dropwise 44.6 g (0.9 equivalent to the collagen-derived peptide) of the acid chloride obtained in above at 40° C. over 2 hours with stirring.

After the addition was completed, the reaction mixture was stirred at 40° C. for 1 hour then heated to 45° c. and stirred for another 1 hour to terminate the reaction. During the reaction, pH of the reaction solution was kept at 9.0 by adding 20% aqueous sodium hydroxide solution little by little. After the reaction was terminated, the reaction solution was poured into 5 l of 5% aqueous sulfuric acid solution to generate a floating precipitate of the acylated product. The floating precipitate of the acylated product was separated from the lower aqueous layer. Thereafter, the acylated product, the floating precipitate, was washed with water by adding water to it, followed by removing the lower aqueous layer. The acylated product thus obtained was neutralized and dissolved with 30% aqueous potassium hydroxide solution and the concentration was adjusted to give 587 g of 30% aqueous solution of a potassium salt of a condensate of non-hydroxyl lanolin fatty acid and collagen-derived peptide. This is abbreviated as NH-collagen-K salt.

Example 2

Synthesis of a sodium salt of a condensate of non-hydroxyl lanolin fatty acid and silk protein-derived peptide Same procedure as in Example 1 was conducted except that the solution obtained by dissolving 150 g of a collagen-derived peptide in 350 g of water was replaced with a solution obtained by dissolving 52.5 g of a silk protein-derived peptide (Promois Silk-700SP, manufactured by Seiwa Kasei Co., Ltd., having an average molecular weight of 350) in 175 g of water and the potassium hydroxide was replaced with a sodium hydroxide to give 301 g of 30% aqueous solution of sodium salt of a condensate of non-hydroxyl lanolin fatty acid and silk protein-derived peptide. This is abbreviated as NH-silk-Na salt.

Example 3

Synthesis of a sodium salt of a condensate of non-hydroxyl lanolin fatty acid and keratin derived peptide Same procedure as in Example 1 was conducted except that the solution obtained by dissolving 150 g of a collagen-derived peptide in 350 g of water was replaced with a solution obtained by dissolving 150 g of keratin-derived peptide (Promois WK-HP, manufactured by Seiwa Kasei Co., Ltd. having an average molecular weight of 1000) in 350 g of water and the potassium hydroxide was replaced with sodium hydroxide to give 613 g of 30% aqueous solution of a sodium salt of a condensate of non-hydroxyl lanolin fatty acid and keratin-derived peptide. This is abbreviated as NH-kertain-Na salt.

Example 4

Synthesis of a triethanolamine salt of a condensate of non-hydroxyl lanolin fatty acid and wheat protein-derived peptide Same procedure as in Example 1 was conducted except that the solution obtained by dissolving 150 g of a collagen-derived peptide in 350 g of water was replaced with 750 g of wheat protein-derived peptide (Hydrotriticum 2000, manufactured by Croda Japan Co., Ltd., having an average molecular weight of 3000, 20% aqueous solution), the amount of acylated chloride to be dropwise added wash changed to 14.9 g and the potassium hydroxide was replaced with triethanolamine to give 503 g of 30% aqueous solution of a triethanolamine salt of a condensate of non-hydroxyl lanolin fatty acid and wheat protein-derived peptide. This is abbreviated as NH-wheat-T salt.

Example 5

Synthesis of a 2-amino-2-methyl-1,3-propanediol salt of a condensate of non-hydroxyl lanolin fatty acid and silk protein-derived peptide Same procedure as in Example 2 was conducted except that the sodium hydroxide, the neutralization agent, was replaced with 2-amino-2-methyl-1,3-propanediol to give 360 g of 25% aqueous solution of a 2-amino-2-methyl-1,3-propanediol salt of a condensate of non-hydroxyl lanolin fatty acid and silk protein-derived peptide. This is abbreviated as NH-silk-2-amino-2-methyl-1,3-propanediol salt.

Example 6

Synthesis of a 2-amino-2-methyl-1,3-propanediol salt of a condensate of non-hydroxyl lanolin fatty acid and casein-derived peptide Same procedure as in Example 1 was conducted except that the solution obtained by dissolving 150 g of a collagen-derived peptide in 350 g of water was replaced with a solution obtained by dissolving 90 g of casein-derived peptide(Promis Milk-P, manufactured by Seiwa Kasei Co., Ltd., having an average molecular weight of 600) in 210 g of water and the potassium hydroxide was replaced with 2-amino-2-methyl-1,3-propanediol to give 510 g of 25% aqueous solution of a 2-amino-2-methyl-1,3-propanediol salt of a condensate of non-hydroxyl lanolin fatty acid and casein-derived peptide. This is abbreviated as NH-casein-2-amino-2-methyl-1,3-propanediol salt.

Example 7

Synthesis of a potassium salt of a condensate of non-hydroxyl lanolin fatty acid and soybean protein-derived peptide Same procedure as in Example 1 was conducted except that the solution obtained by dissolving 150 g of a collagen-derived peptide in 350 g of water was replaced with 750 g of soybean protein-derived peptide(Hydrosoy 2000SF, manufactured by Croda Japan Co., Ltd., having an average molecular weight of 4000, 20% aqueous solution) and the amount of acylated chloride to be dropwise added was changed to 11.2 g to give 710 g of 20% aqueous solution of a potassium salt of a condensate of non-hydroxyl lanolin fatty acid and soybean protein-derived peptide. This is abbreviated as NH-soybean-K salt.

Comparative Example 1

Synthesis of a potassium salt of a condensate of myristic acid and collegan-derived peptide At 55° C. was molten 228 g (1 mol) of myristic acid (NAAA142, manufactured by NOF Corporation). To this was added dropwise 69 g (0.5 mol) of phosphorus trichloride over about 30 minutes. The mixture was stirred at 55–60° C. for 3 hours and allowed to stand for 8 hours. Then the lower layer containing of phosphorous acid was removed to give a crude acid chloride. The crude acid chloride was distilled in a glass distillation apparatus to give 230 g of an acid chloride.

Into a solution obtained by dissolving 150 g of a collegan-derived peptide (CCP-100P manufacture by Nikko Chemicals Co., Ltd., having an average molecular weight of 1,000) in 350 g of water was added dropwise 33.3 g (0.9 equivalent to the collagen-derived peptide) of the acid chloride obtained in above at 40° C. over 2 hours with stirring.

After the dropwise addition was completed, the reaction mixture was stirred at 40° C. for 1 hour, then heated to 45° C. and stirred for another 1 hour to terminate the reaction. During the reaction, pH of the reaction solution was kept at 9.0 by adding 20% aqueous sodium hydroxide solution little by little. After the reaction was terminated, the reaction solution was poured into 5 l of 5% aqueous sulfuric acid solution to generate a floating precipitate of the acylated product. The floating precipitate of the acylated product was separated from the lower aqueous layer.

Thereafter, the acylated product, the floating precipitate, was washed with water by adding water to it and then removing the lower aqueous layer. The acylated product thus obtained was neutralized and dissolved with 30% aqueous potassium hydroxide solution and the concentration was adjusted to give 590 g of 30% aqueous solution of a potassium salt of a condensate of myristic acid and collegan-derived peptide. This is abbreviated as myristic-collagen-K salt.

Comparative Example 2

Synthesis of a sodium salt of a condensate of a lanolin fatty acid and keratin-derived peptide At 55° C. was molten 330 g (1 mol) of a lanolin fatty acid (Lanolin Fatty Acid A, manufactured by Nippon Fine Chemical Co., Ltd. containing 24.6% by weight of the iso-type fatty acid of formula (I), 31.0% by weight of the anteiso-type fatty acid of formula (II), 13.3% by weight of the normal type fatty acid of formula (III), and 18.5% by weight of hydroxyl fatty acids, and the average carbon number of said iso-type fatty acid, anteio-type fatty acid and normal type fatty acid being 21.1). To this was added dropwise 69 g (0.5 mol) of phosphorus trichloride over about 30 minutes. The mixture was stirred at 55–60° C. for 3 hours and allowed to stand for 8 hours. Then the lower layer containing of phosphorous acid was removed to give a crude acid chloride. The crude acid chloride was distilled in a glass distillation apparatus to give 270 g of an acid chloride.

Into a solution obtained by dissolving 150 g of a keratin-derived peptide(Promois WK-HP, manufactured by Seiwa Kasei Co., Ltd., having an average molecular weight of 1,000) in 350 g of water was added dropwise 47 g (0.9 equivalent to the keratin-derived peptide) of the acid chloride obtained in above at 40° C. over 2 hours with stirring.

After the addition was completed, the reaction mixture was stirred at 40° C. for 1 hour, then heated to 45° C. and stirred for another 1 hour to terminate the reaction. During the reaction, pH of the reaction solution was kept at 9.0 by adding 20% aqueous sodium hydroxide solution little by little. After the reaction was terminated, the reaction solution was poured into 5 l of 5% aqueous sulfuric acid solution to generate a floating precipitate of the acylated product. The floating precipitate of the acylated product was separated from the lower aqueous layer. Thereafter, the acylated product, the floating precipitate, was washed with water by adding water to it and then removing the lower aqueous layer. The acylated product thus obtained was neutralized and dissolved with 30% aqueous sodium hydroxide solution, and the concentration was adjusted to give 580 g of 30% aqueous solution of a sodium salt of a condensate of a lanolin fatty acid and keratin-derived peptide. This is abbreviated as lanolin-keratin-Na salt.

Comparative Example 3

Synthesis of triethanolamine salt of a condensate of a isostearic acid and wheat protein-derived peptide To 55° C. was heated 291 g (1 mol) of an isostearic acid (Isostearic Acid PK, manufactured by Kokyu Alcohol Kogyo Co., Ltd.). To this was added dropwise 69 g (0.5 mol) of phosphorus trichloride over above 30 minutes. The mixture was stirred at 55–60° C. for 3 hours and allowed to stand for 8 hours. Then the lower layer containing of phosphorous acid was removed to give a crude acid chloride. The crude acid chloride was distilled in a glass distillation apparatus to give 280 g of a an acid chloride.

Into 750 g of a wheat protein-derived peptide (Hydrotriticum 2000, manufactured by Croda Japan Co., Ltd., having an average molecular weight of 3,000, 20% aqueous solution), was added dropwise 13.9 g (0.9 g equivalent to the wheat protein-derived peptide) of the acid chloride obtained in above at 40° C. over 2 hours with stirring.

After the addition was completed, the reaction mixture was stirred at 40° C. for 1 hour, then heated to 45° C. and stirred for another 1 hours to terminate the reaction. During the reaction, pH of the reaction solution was kept at 9.0 by adding 20% aqueous sodium hydroxide solution little by little. After the reaction was terminated, the reaction solution was poured into 5 l of 5% aqueous sulfuric acid solution to generate a floating precipitate of the acylated product. The floating precipitate of the acylated product was separated from the lower aqueous layer. Thereafter, the acylated product, the floating precipitate, was washed with water by adding water to it and then removing the lower aqueous layer. The acylated product thus obtained was neutralized with triethanolamine and dissolved in water, and the concentration was adjusted to give 530 g of 30% aqueous solution of a triethanolamine salt of a condensate of a isostearic acid and wheat-derived peptide. This is abbreviated as isoste-wheat-T salt.

Comparative Example 4

Synthesis of a 2-amino-2-methyl-1,3-propanediol salt of a condensate of a isostearic acid and silk protein-derived peptide To a solution obtained by dissolving 52.5 g of silk protein-derived peptide (Promois Silk-700SP, manufactured by Seiwa Kasei Co., Ltd., having an average molecular weight of 350) in 175 g of water was added dropwise 41.8 g (0.9 equivalent to the silk protein-derived peptide) of the acid chloride obtained in Comparative example 3 at 40° C. over 2 hours with stirring.

After the addition was completed, the reaction mixture was stirred at 40° C. for 1 hour, then heated to 45° C. and stirred for another 1 hour to terminate the reaction. During the reaction, pH of the reaction solution was kept at 9.0 by adding 20% aqueous sodium hydroxide solution little by little. After the reaction was terminated, the reaction solution was poured into 5 l of 5% aqueous sulfuric acid solution to generate a floating precipitate of the acylated product. The floating precipitate of the acylated product was separated from the lower aqueous layer. Thereafter, the acylated product, the floating precipitate, was washed with water by adding water to it and then removing the lower aqueous layer. The acylated product thus obtained was neutralized with 2-amino-2-methyl-1,3-propanediol and dissolved in water, and the concentration was adjusted to give 368 g of 25% aqueous solution of a 2-amino-2-methyl-1,3-propanediol salt of a condensate of a isostearic acid and silk-derived peptide. This is abbreviated as isoste-silk-2-amino-2-methyl-1,3-propanediol salt.

Example 8-9 and Comparative Example 5-6

Four kinds of shampoo compositions shown in Table 1 were prepared. The gloss and moist feel of the hair which was treated with each shampoo composition and dried were evaluated.

Method of evaluation

The glass and moist feel of hair were sensory evaluated by a panel consisting of 10 female sensory-panelists who were instructed to use-test the shampoo compositions. The results according to the following criteria are shown in Table 1.

○: The number of panelists answering "good" is 7–10.
Δ: The number of panelists answering "good" is 4–6.
X: The number of panelists answering "good" is 0–3.

TABLE 1

|  | Example | | Comparative Example | |
| --- | --- | --- | --- | --- |
| Ingredient | 8 | 9 | 5 | 6 |
| Triethanolamine Polyoxyethylene (3) laurylether sulfate (40%) *1 | 20.0 | 20.0 | 20.0 | 30.0 |
| Sodium laurylsulfate (30%) *2 | 15.0 | 15.0 | 15.0 | 20.0 |
| NH-collagen-K salt (30%) | 15.0 | 0 | 0 | 0 |
| NH-keratin-Na salt (30%) | 0 | 15.0 | 0 | 0 |
| Myristic-collagen-K salt (30%) | 0 | 0 | 15.0 | 0 |
| Lauric acid diethanolamide *3 | 4.0 | 4.0 | 4.0 | 4.0 |
| Citric acid | 0.1 | 0.1 | 0.1 | 0.1 |
| EDTA-2-Na *4 | 0.1 | 0.1 | 0.1 | 0.1 |
| Antiseptic | q.s. | q.s | q.s. | q.s. |
| Sterilized ion-exchanged Water | Balance | Balance | Balance | Balance |
| Gloss | ○ | ○ | Δ | X |
| Moist feel | ○ | ○ | Δ | X |

*1: Emal 20T, manufactured by Kao Corporation
*2: Emal 2F, manufactured by Kao Corporation
*3: Coperlan LD, manufactured by Henkel Hakusui Co., Ltd.
*4: Chelest 2BS, manufactured by Chelest Corporation The numbers in the Table indicate the compounded amounts (part by weight) of each ingredient.

The term "Balance" in the Table means the required amount to make the total amount 100 parts by weight.

The above annotations are also applied to all other Tables in this specification.

Example 10-11 and Comparative Example 7-8

Four kinds of hair rinse compositions shown in Table 2 were prepared. The gloss and moist feel of the hair treated with each hair rinse composition and dried were evaluated.

Method of evaluation

The gloss and moist feel of hair were sensory evaluated by a panel consisting of 10 female sensory-panelists who were instructed to use-test the hair rinse compositions. The results according to the same criteria as in Example 8-9 are shown in Table 2.

TABLE 2

|  | Example | | Comparative Example | |
| --- | --- | --- | --- | --- |
| Ingredient | 10 | 11 | 7 | 8 |
| Stearyl trimethylammonium chloride *1 | 3.0 | 3.0 | 3.0 | 3.0 |
| Distearyl dimethylammonium chloride *2 | 2.0 | 2.0 | 2.0 | 2.0 |
| NH-silk-2-amino-2-methyl-1,3-propanediol salt (25%) | 3.0 | 0 | 0 | 0 |
| NH-casein-2-amino-2-methyl-1,3-propanediol salt (25%) | 0 | 3.0 | 0 | 0 |
| Isoste-silk-2-amino-2-methyl-1,3-propanediol salt (25%) | 0 | 0 | 3.0 | 0 |
| Cetanol *3 | 2.5 | 2.5 | 2.5 | 2.5 |
| 1,3-butylene glycol | 4.0 | 4.0 | 4.0 | 4.0 |
| Antiseptic | q.s. | q.s. | q.s. | q.s. |
| Sterilized ion-exchanged Water | Balance | Balance | Balance | Balance |
| Gloss | ○ | ○ | Δ | Δ |
| Moist feel | ○ | ○ | Δ | X |

*1: Dehyquart B, manufactured by Henkel Hakusui Co., Ltd.
*2: Dehyquart TA100, manufactured by Henkel Hakusui Co., Ltd.
*3: Kalcol 6870, manufactured by Kao Corporation Example 12-13 and Comparative Example 9-10

Four kinds of cold permanent wave lotions shown in Table 3 were prepared. The moist feel of the hair treated with each cold permanent wave lotion was evaluated.

Method of evaluation

The moist feel of hair were sensory evaluated by a panel consisting of 10 female sensory-panelists who were instructed to be subjected to permanent wave treatment using the cold permanent wave lotions shown in Table 3 and to evaluate the moist feel of hair after drying. The results according to the same criteria as in Example 8–9 are shown in Table 3.

TABLE 3

|  | Example | | Comparative Example | |
| --- | --- | --- | --- | --- |
| Ingredient | 12 | 13 | 9 | 10 |
| The first agent | | | | |
| Ammonium thioglycolate (50%) *1 | 12.0 | 12.0 | 12.0 | 12.0 |
| Aqueous ammonia (28%) | 3.5 | 3.5 | 3.5 | 3.5 |
| NH-silk-Na salt (30%) | 3.0 | 0 | 0 | 0 |
| NH-keratin-Na salt (30%) | 0 | 3.0 | 0 | 0 |
| Lanolin-keratin-Na salt (30%) | 0 | 0 | 3.0 | 0 |
| EDTA-2-Na *2 | 0.1 | 0.1 | 0.1 | 0.1 |
| Polyoxyethylene cetylether *3 | q.s. | q.s. | q.s. | q.s. |
| Sterilized ion-exchanged Water | Balance | Balance | Balance | Balance |
| The second agent | | | | |
| Sodium bromate *4 | 6.0 | 6.0 | 6.0 | 6.0 |
| Citric acid | 0.01 | 0.01 | 0.01 | 0.01 |
| Trisodium citrate | 0.3 | 0.3 | 0.3 | 0.3 |
| Sterilized ion-exchanged Water | Balance | Balance | Balance | Balance |
| Moist feel | ◯ | ◯ | Δ | X |

*1: 50% Ammonium thioglycolate, manufactured by Sasaki Chemical Co., Ltd.
*2: Chelest 2BS, manufactured by Chelest Corporation
*3: Nissan nonion P-213, manufactured by NOF Corporation
*4: Sodium bromate, manufactured by Otsuka Chemical Co., Ltd.

Example 14-15 and Comparative Example 11-12

Four kinds of hair blow compositions shown in Table 4 were prepared. The gloss and moist feel of the hair treated with each hair blow composition and dried were evaluated.

Method of evaluation

The gloss and moist feel of hair were sensory evaluated by a panel consisting of 10 female sensory-panelists who were instructed to use-test and hair blow compositions. The results according to the same criteria as in Example 8-9 are shown in Table 4.

TABLE 4

|  | Example | | Comparative Example | |
| --- | --- | --- | --- | --- |
| Ingredient | 14 | 15 | 11 | 12 |
| Stearyl trimethylammonium chloride *1 | 0.4 | 0.4 | 0.4 | 0.4 |
| NH-silk-2-amino-2-methyl-1,3-propanediol salt (25%) | 3.0 | 0 | 0 | 0 |
| NH-casein-2-amino-2-methyl-1,3-propanediol salt (25%) | 0 | 3.0 | 0 | 0 |
| Isoste-silk-2-amino-2-methyl-1,3-propanediol salt (25%) | 0 | 0 | 3.0 | 0 |

TABLE 4-continued

|  | Example | | Comparative Example | |
| --- | --- | --- | --- | --- |
| Ingredient | 14 | 15 | 11 | 12 |
| Polyvinyl pirrolidone *2 | 1.0 | 1.0 | 1.0 | 1.0 |
| Ethanol | 70.0 | 70.0 | 70.0 | 70.0 |
| Perfume | q.s. | q.s. | q.s. | q.s. |
| Sterilized ion-exchanged Water | Balance | Balance | Balance | Balance |
| Gloss | ◯ | ◯ | ◯ | Δ |
| Moist feel | ◯ | ◯ | Δ | X |

*1: Dehyquart B, manufactured by Henkel Hakusui Co., Ltd.
*2: PVP K30, manufactured by ISP Japan Co., Ltd.

Example 16-17 and Comparative Example 13-14

Four kinds of skin soap compositions shown in Table 5 were prepared. The moist feel after using each skin soap composition was evaluated.

Method of evaluation

The moist feel of skin were sensory evaluated by a panel consisting of 10 female sensory-panelists who were instructed to use-test the skin soap compositions. The results according to the same criteria as in Example 8-9 are shown in Table 5.

TABLE 5

|  | Example | | Comparative Example | |
| --- | --- | --- | --- | --- |
| Ingredient | 16 | 17 | 13 | 14 |
| NH-soybean-K salt (20%) | 60.0 | 0 | 0 | 0 |
| NH-wheat-T salt (30%) | 0 | 40.0 | 0 | 0 |
| Myristic-collagen-K salt (30%) | 0 | 0 | 40.0 | 0 |
| Isoste-wheat-T salt (30%) | 0 | 0 | 0 | 40.0 |
| Coconut fatty acid diethanolamide *1 | 2.0 | 2.0 | 2.0 | 2.0 |
| 2-Alkyl-N-carboxymethyl-N-hydroxyethyl imidazolinium betaine *2 | 2.0 | 2.0 | 2.0 | 2.0 |
| Lauric acid *3 | 4.0 | 4.0 | 4.0 | 4.0 |
| Polyethyleneglycol monostearate *4 | 2.0 | 2.0 | 2.0 | 2.0 |
| Propyleneglycol | 7.0 | 7.0 | 7.0 | 7.0 |
| Triethanolamine | 3.0 | 3.0 | 3.0 | 3.0 |
| Sodium chloride | 1.0 | 1.0 | 1.0 | 1.0 |
| Urea | 0.7 | 0.7 | 0.7 | 0.7 |
| Antiseptic | q.s. | q.s. | q.s. | q.s. |
| Perfume | q.s. | q.s. | q.s. | q.s. |
| Sterilized ion-exchanged Water | Balance | Balance | Balance | Balance |
| Moist feel | ◯ | ◯ | Δ | Δ |

*1: Annon PK-02S, manufactured by Kao Corporation
*2: Nissan Anon GLM-R, manufactured by NOF Corporation
*3: Lauric acid S, manufactured by Nippon Fine Chemical Co., Ltd.
*4: Emanon 3199, manufactured by Kao Corporation Example 18 and Comparative Example 15-16

Three kinds of shampoo compositions shown in Table 6 were prepared. Hair was washed with each shampoo composition and the washed hair was evaluated in manageability, gloss, moisture and combability (response to hair to combing).

As the acylated peptide or a salt thereof, the potassium salt of a condensate of non-hydroxyl lanolin fatty acid and soybean protein-derived peptide obtained in Example 7 was added to the composition of Example 18. In place of the potassium salt of a condensate of non-hydroxyl lanolin fatty acid and soybean protein-derived peptide, the potassium salt of a condensate of myristic acid and collagen-derived peptide obtained in Comparative example 1 was added to the composition of Comparative example 15. No acylated peptide or a salt thereof was added to the composition of Comparative example 16.

TABLE 6

| Ingredient | Example 18 | Comparative Example 15 | Comparative Example 16 |
|---|---|---|---|
| NH-soybean-K salt (20%) | 3.0 | 0 | 0 |
| Myristic-collagen-K salt (30%) | 0 | 2.0 | 0 |
| Sodium-N-lauroyl sarcosinate (30%) | 25.0 | 25.0 | 25.0 |
| Cocamide propyl Betaine | 5.0 | 5.0 | 5.0 |
| Coconut fatty acid diethanolamide | 3.0 | 3.0 | 3.0 |
| Methyl parahydroxybenzoate | 0.3 | 0.3 | 0.3 |
| EDTA-2Na | 0.2 | 0.2 | 0.2 |
| Perfume | q.s. | q.s. | q.s. |
| Sterilized ion-exchanged Water | Balance | Balance | Balance |

Method of evaluation

Hair bundles having a length of 15 cm and weighing 1 g were prepared from healthy black hair from women in their twenties. Each hair bundle was washed with 1 g of each shampoo composition shown in Table 6. Thereafter, the hair bundles were rinsed with hot water and dried with a hair drier. After repeating this shampoo treatment five times, the manageability, gloss, moisture and combability of the hair were evaluated by a panel consisting of 10 female sensory-panelists who were instructed to use-test the shampoo compositions according to the criteria of the 5-stage scoring system described below. The results are shown in Table 7 as an average of the 10 panelists.

Criteria
5: Excellent
4: Good
3: Fair
2: Bad
1: Very bad

TABLE 7

| Evaluation | Example 18 | Comparative Example 15 | Comparative Example 16 |
|---|---|---|---|
| Gloss | 3.4 | 2.8 | 2.0 |
| Moisture | 3.6 | 2.6 | 1.7 |
| Combability | 3.5 | 3.0 | 1.5 |
| Manageability | 3.6 | 3.0 | 1.6 |

As shown in Table 7, the hair treated with the shampoo solution of Example 18 is superior in satisfying all the evaluated conditions; the manageability, gloss, moisture and combability, to the hair treated with the shampoo solution of Comparative example 15 or Comparative example 16. That is, the results in Table 7 clearly show that the potassium salt of acylated peptide obtained by condensing a non-hydroxyl lanolin fatty acid with a soybean protein-derived peptide is excellent in the manageability, the effect of giving hair moisture and gloss and the effect of improving combability of hair.

Example 19 and Comparative Example 17-18

Three kinds of hair treatment creams shown in Table 8 were prepared. Each hair treatment cream was applied to hair and then the hair was evaluated in manageability, gloss, moisture and combability.

As the acylated peptide or a salt thereof, the sodium salt of a condensate of non-hydroxyl lanolin fatty acid and keratin-derived peptide obtained in Example 3 was added to the composition of Example 19. In place of the sodium salt of a condensate of non-hydroxyl lanolin fatty acid and keratin-derived peptide, the sodium salt of a condensate of lanolin fatty acid and keratin-derived peptide obtained in Comparative example 2 was added to the composition of Comparative example 17. No acylated peptide or a salt thereof was added to the composition of Comparative example 18.

TABLE 8

| Ingredient | Example 19 | Comparative Example 17 | Comparative Example 18 |
|---|---|---|---|
| NH-keratin-Na salt (30%) | 2.0 | 0 | 0 |
| Lanolin-keratin-Na salt (30%) | 0 | 2.0 | 0 |
| Stearamidoethyl diethylamine | 3.0 | 3.0 | 3.0 |
| Cetanol | 5.5 | 5.5 | 5.5 |
| Phosphoric acid | 0.4 | 0.4 | 0.4 |
| Diglycerine | 2.0 | 2.0 | 2.0 |
| Hydrolyzed keratin (25%) *1 | 2.4 | 2.4 | 2.4 |
| Mixture of parahydroxybenzoate and phenoxyethanol *2 | 0.3 | 0.3 | 0.3 |
| EDTA-2Na | 0.1 | 0.1 | 0.1 |
| Perfume | q.s. | q.s. | q.s. |
| Sterilized ion-exchanged Water | Balance | Balance | Balance |

*1: Promois WK, manufactured by Seiwa Kasei Co., Ltd.
*2: Seisept H, manufactured by Seiwa Kasei Co., Ltd.

Method of evaluation

Hair bundles having a length of 15 cm and weighing 1 g were prepared from healthy black hair from women in their twenties. The hair bundles were washed with a commercial shampoo. Then, each hair bundle was coated with 2 g of each hair treatment cream in Table 8 and rinsed with hot water. After repeating the treatment with shampoo and hair treatment cream five times, the manageability, gloss, moisture and combability of the hair were evaluated by a panel consisting of 10 female sensory-panelists who were instructed to use-test according to the criteria of the 5-stage scoring system described in Example 18. The results are shown in Table 9 as an average of the 10 panelists.

TABLE 9

| Evaluation | Example 19 | Comparative Example 17 | Comparative Example 18 |
|---|---|---|---|
| Gloss | 4.0 | 3.0 | 1.8 |
| Moisture | 3.5 | 2.6 | 2.1 |
| Combability | 4.0 | 3.1 | 1.8 |
| Manageability | 3.8 | 3.4 | 1.7 |

As shown in Table 9, the hair treated with the hair treatment cream of Example 19 is superior in satisfying all the evaluated conditions; the manageability, gloss, moisture and combability, to the hair treated with the hair treatment cream of Comparative example 17 or Comparative example 18. That is, the results in Table 9 clearly show that the sodium salt of acylated peptide obtained by condensing a non-hydroxyl lanolin fatty acid with a keratin-derived peptide is excellent in the mangeability, the effect of giving the hair moisture and gloss and the effect of improving combability of hair.

Although the sodium salt of a condensate of lanolin fatty acid and keratin-derived peptide obtained in Comparative example 2 exhibits the manageability, the effect of giving the hair moisture and gloss and the effect of improving combability of hair, the results in Table 9 indicate superiority of the sodium salt acylated peptide obtained by condensing a non-hydroxyl lanolin fatty acid with a keratin-derived peptide in said effects.

Example 20 and Comparative Example 19–20

Three kinds of the first agents for permanent wave shown in Table 10 were prepared. Hair bundles were subjected to permanent wave treatment using the first agents and the second agent for permanent wave consisting of 6% aqueous sodium bromate solution. The treated hair bundles were evaluated in gloss and moisture of hair by sensory inspection.

As the acylated peptide or a salt thereof, the potassium salt of a condensate of non-hydroxyl lanolin fatty acid and collagen-derived peptide obtained in Example 1 was added to the composition of Example 20. In place of the potassium salt of a condensate of non-hydroxyl lanolin fatty acid and collagen-derived peptide, the potassium salt of a condensate of myristic acid and collagen-derived peptide obtained in Comparative example 1 was added to the composition of Comparative example 19. No acylated peptide or a salt thereof was added to the composition of Comparative example 20.

TABLE 10

| Ingredient | Example 20 | Comparative Example 19 | Comparative Example 20 |
|---|---|---|---|
| NH-collagen-K salt (30%) | 1.0 | 0 | 0 |
| Myristic-collagen-K salt (30%) | 0 | 1.0 | 0 |
| Ammonium thioglycolate (50%) | 12.0 | 12.0 | 12.0 |
| Monoethanolamine | 0.8 | 0.8 | 0.8 |
| Polyoxyethylene (25) cetylether | 1.5 | 1.5 | 1.5 |
| Coconut fatty acid diethanolamide | 0.3 | 0.3 | 0.3 |
| EDTA-2Na | 0.1 | 0.1 | 0.1 |
| Aqueous ammonia (25%) | 2.5 | 2.5 | 2.5 |
| Perfume | q.s. | q.s. | q.s. |
| Sterilized ion-exchanged Water | Balance | Balance | Balance |

Method of evaluation:

Hair bundles having a length of 20 cm and weighing 1 g were prepared from healthy black hair obtained from women in their twenties. The hair bundles were washed with a commercial shampoo. Then, each hair bundle was fixed at the both ends with rubber bands after winding around a rod having a diameter of 1 cm and a length of 8 cm. Thereafter, each 2 ml of the first agents for permanent wave shown in Table 10 was applied onto each hair bundle, which was then covered with plastic film and allowed to stand for 15 minutes. All of the hair bundles were then washed in running water for 10 seconds, applied with each 2 ml of the second agent for permanent wave, covered with plastic film and allowed to stand for 15 minutes. The hair bundles were washed gently in running water for 30 seconds, dried in a drying oven at 50° C. for 20 minutes and removed from the rods.

Thereafter, gloss and moisture of hair were evaluated by a panel consisting of 10 female sensory-panelists who were instructed to use-test according to the criteria of the 5-stage scoring system described in Example 18. The results are shown in Table 11 as an average of the 10 panelists.

TABLE 11

| Evaluation | Example 20 | Comparative Example 19 | Comparative Example 20 |
|---|---|---|---|
| Gloss | 4.2 | 3.0 | 0.9 |
| Moisture | 3.7 | 2.8 | 1.5 |

As shown in Table 11, the hair subjected to a permanent wave treatment using the first agent for permanent wave of Example 20 containing the potassium salt of a condensate of non-hydroxyl lanolin fatty acid and collagen-derived peptide is superior in satisfying all the evaluated conditions; gloss and moisture, to the hair subjected to a permanent wave treatment using the first agent for permanent wave of Comparative example 19 or Comparative example 20. That is, the results in Table 11 clearly show that the potassium salt of acylated peptide obtained by condensing a non-hydroxyl lanolin fatty acid with a collagen-derived peptide is excellent in the effect of giving the hair moisture and gloss.

Example 21 and Comparative Example 21–22

Three kinds of the first agents for hair dyeing shown in Table 12 and the second agent for hair dyeing shown in Table 13 were prepared. Hair was subjected to a hair dyeing treatment using each of the first agents and the second agent and the treated hair was evaluated in gloss, moisture and combability of hair by sensory inspection.

As the acylated peptide or a salt thereof, the 2-amino-2-methyl-1,3-propanediol salt of a condensate of non-hydroxyl lanolin fatty acid and silk protein-derived peptide obtained in Example 5 was added to the composition of Example 21. In place of the 2-amino-2-methyl-1,3-propanediol salt of a condensate of non-hydroxyl lanolin fatty acid and silk protein-derived peptide, the 2-amino-2-methyl-1,3-propanediol salt of a condensate of a isostearic acid and silk protein-derived peptide obtained in Comparative example 4 was added to the composition of Comparative example 21. No acylated peptide or a salt thereof was added to the composition of Comparative example 22.

TABLE 12

The First Agent

| Ingredient | Example 21 | Comparative Example 21 | Comparative Example 22 |
|---|---|---|---|
| NH-silk-2-amino-2-methyl-1,3-propanediol salt(25%) | 10.0 | 0 | 0 |
| Isoste-silk-2-amino-2-methyl-1,3-propanediol salt(25%) | 0 | 10.0 | 0 |
| p-Phenylenediamine | 0.72 | 0.72 | 0.72 |
| p-Aminophenol | 0.34 | 0.34 | 0.34 |
| Sodium laurylsulfate | 10.5 | 10.5 | 10.5 |

TABLE 12-continued

The First Agent

| | Example | Comparative Example | |
|---|---|---|---|
| Ingredient | 21 | 21 | 22 |
| Coconut fatty acid diethanolamide | 5.0 | 5.0 | 5.0 |
| Polyoxyethylene nonyl-phenylether | 3.0 | 3.0 | 3.0 |
| glycerine | 2.0 | 2.0 | 2.0 |
| EDTA-2Na | 0.3 | 0.3 | 0.3 |
| Citric acid | 0.1 | 0.1 | 0.1 |
| Sterilized ion-exchanged Water | Balance | Balance | Balance |

TABLE 13

The Second Agent

| Aqueous hydrogen peroxide(35%) | 8.0 |
|---|---|
| Cetanol | 0.3 |
| Polyoxyethylenecetylether | 0.2 |
| Sterilized ion-exchanged Water | Balance |

Method of evaluation:

Hair bundles having a length of 15 cm and weighing 1 g were prepared from healthy black hair obtained from women in their twenties. The hair bundles were washed with a commercial shampoo. Each hair bundle was hair-dyed using 2 g of mixed liquid obtained by mixing equal amounts of each of the first agent of Table 12 and the second agent of Table 13. Thereafter, the hair bundle was rinsed with warm water, hair-dyed again with 2 g of the mixed liquid, washed with 2% aqueous solution of polyoxyethylene nonylphenylether and then dried with a hair drier. Thereafter, gloss, moisture and combability of the hair bundle were evaluated by a panel consisting of 10 female sensory-panelists who were instructed to use-test according to the criteria of the 5-stage scoring system described in Example 18. The results are shown in Table 14 as an average of the 10 panelists.

TABLE 14

| | Example | Comparative Example | |
|---|---|---|---|
| Evaluation | 21 | 21 | 22 |
| Gloss | 4.2 | 2.8 | 1.4 |
| Moisture | 3.5 | 2.4 | 1.0 |
| Combability | 3.8 | 2.3 | 1.5 |

As shown in Table 14, the hair subjected to a hair-dyeing treatment using the hair-dye of Example 21 containing the 2-amino-2-methyl-1,3-propanediol salt of a condensate of non-hydroxyl lanolin fatty acid and silk protein-derived peptide, is superior in satisfying all the evaluated conditions; gloss, moisture and combability, to the hair subjected to a hair-dyeing treatment using the hair-dye of Comparative example 21 or Comparative example 22. That is, the results in Table 14 clearly show that the 2-amino-2-methyl-1,3-propanediol salt of acylated peptide obtained by condensing non-hydroxyl lanolin fatty acid with a silk protein-derived peptide is excellent in the effect of giving hair moisture and gloss and in the effect of improving the combability of the hair.

Example 22 and Comparative Examples 23–24

Three kinds of body-shampoos shown in Table 15 were prepared. After washing a human body with each body-shampoo, smoothness and moistness of skin were evaluated.

As the acylated peptide or a salt thereof, the triethanolamine salt of a condensate of non-hydroxyl lanolin fatty acid and wheat protein-derived peptide obtained in Example 4 was added to the composition of Example 22. In place of the triethanolamine salt of a condensate of non-hydroxyl lanolin fatty acid and wheat protein-derived peptide, the trithanolamine salt of a condensate of a isostearic acid and wheat protein-derived peptide obtained in Comparative example 3 was added to the composition of Comparative example 23. No acylated peptide or a salt thereof was added to the composition of Comparative example 24.

TABLE 15

| | Example | Comparative Example | |
|---|---|---|---|
| Ingredient | 22 | 23 | 24 |
| NH-wheat-T salt(30%) | 2.0 | 0 | 0 |
| Isoste-wheat-T salt(30%) | 0 | 2.0 | 0 |
| Triethanolamine-coco-hydrolized animal protein(35%) | 10.0 | 10.0 | 10.0 |
| 2-Alkyl-N-carboxymethyl-N-hydroxyethyl imidazolinium betaine (30%) | 20.0 | 20.0 | 20.0 |
| Sodium-N-cocoyl-N-methyltaurate (30%) | 15.0 | 15.0 | 15.0 |
| Lauric acid diethanolamide | 4.0 | 4.0 | 4.0 |
| Polyethyleneglycol distearate(140E.O.) | 0.5 | 0.5 | 0.5 |
| Ethyleneglycol monostearate | 0.5 | 0.5 | 0.5 |
| Mixture of parahydroxybenzoate and phenoxyethanol *1 | 0.3 | 0.3 | 0.3 |
| EDTA-2Na | 0.1 | 0.1 | 0.1 |
| Sterilized ion-exchange Water | Balance | Balance | Balance |

*1: Seisept H, manufactured by Seiwa Kasei Co., Ltd.

Method of evaluation:

Without shown the contents in Table 15, 5 male and 5 female sensory-panelists were instructed to use each body shampoo for 3 days and to evaluate the smoothness and moistness of skin according to the following criteria.

2: Excellent

1: Good

0: Bad

The results are shown in Table 16 as an average of the 10 panelists.

TABLE 16

| | Example | Comparative Example | |
|---|---|---|---|
| Evaluation | 22 | 23 | 24 |
| Smoothness | 2.0 | 1.0 | 0.0 |
| Moistness | 2.0 | 1.0 | 0.0 |

As shown in Table 16, all of the ten panelists answered that the body-shampoo of Example 22 containing the triethanolamine salt of a condensate of non-hydroxyl lanolin fatty acid and wheat protein-derived peptide is better in the effects of giving smoothness and moistness to the skin than the body-shampoo of Comparative example 23 or Comparative example 24. That is, the results in Table 16 clearly show that the triethanolamine salt of acylated peptide obtained by condensing non-hydroxyl lanolin fatty acid with a wheat protein-derived peptide is excellent in the effects of giving the skin smoothness and moistness, and is superior, in the effects, to the triethanolamine salt of acylated peptide obtained by condensing isostearic acid with a wheat protein-derived peptide.

Example 23 and Comparative Examples 25–26

Three kinds of hand & nail creams shown in Table 17 were prepared. After washing hands, each hand & nail cream was applied on the washed hands and the luster, moistness and smoothness of the skin were evaluated.

As the acylated peptide or a salt thereof, the sodium salt of a condensate of non-hydroxyl lanolin fatty acid and keratin-derived peptide obtained in Example 3 was added to the composition of Example 23. In place of the sodium salt of a condensate of non-hydroxyl lanolin fatty acid and keratin-derived peptide, the sodium salt of a condensate of lanolin fatty acid and keratin-derived peptide obtained in Comparative example 2 was added to the composition of Comparative example 25. No acylated peptide or a salt thereof was added to the composition of Comparative example 26.

TABLE 17

| Ingredient | Example 23 | Comparative Example 25 | Comparative Example 26 |
|---|---|---|---|
| NH-keratin-Na salt(30%) | 4.0 | 0 | 0 |
| Lanolin-keratin-Na salt(30%) | 0 | 4.0 | 0 |
| Isopropyl isostearate | 6.0 | 6.0 | 6.0 |
| Cetanol | 4.0 | 4.0 | 4.0 |
| Stearic acid | 3.3 | 3.3 | 3.3 |
| Stearyl alcohol | 2.7 | 2.7 | 2.7 |
| Sodium cetylsulfate | 0.7 | 0.7 | 0.7 |
| Dimethylpolysiloxane | 0.5 | 0.5 | 0.5 |
| Mixture of polyoxyethylene laurylethers(10EO, 15EO, 25EO) 1* | 1.0 | 1.0 | 1.0 |
| Polyoxyethylene(25) cetylether | 0.5 | 0.5 | 0.5 |
| Polyoxyethylene(6) cetylether | 0.6 | 0.6 | 0.6 |
| Methyl parahydroxybenzoate | 0.3 | 0.3 | 0.3 |
| Butyl parahydroxybenzoate | 0.1 | 0.1 | 0.1 |
| Propyleneglycol | 6.0 | 6.0 | 6.0 |
| Sorbitol | 1.0 | 1.0 | 1.0 |
| Sterilized ion-exchanged Water | Balance | Balance | Balance |

*1: Ayacol PL-50, manufactured by Seiwa Kasei Co., Ltd.

Method of evaluation:

Five male and 5 female sensory-panelists were instructed to wash their hands with 20% aqueous potassium coconate soap solution and then to wash their hands with water. Thereafter, they were instructed to apply a spoonful of each hand & nail cream of Table 18 (amounts of the hand & nail creams being measured with a measuring spoon having the volume of 1 ml and the amounts being about 1 g) by extending and rubbing the cream into the backs of their hands, and to evaluate the smoothness, moistness and luster of the skin applied with the cream according to the same criteria of the 3-stage scoring system as in Example 22. The results are shown in Table 18 as an average of the 10 panelists.

TABLE 18

| Evaluation | Example 23 | Comparative Example 25 | Comparative Example 26 |
|---|---|---|---|
| Smoothness | 2.0 | 1.0 | 0.0 |
| Moistness | 2.0 | 1.0 | 0.0 |
| Luster | 1.8 | 1.2 | 0.0 |

As shown in Table 18, almost all of the panelists answered that the hand & nail cream of Example 23 containing the sodium salt of a condensate of non-hydroxyl lanolin fatty acid and keratin-derived peptide is better in the effects of giving smoothness, moistness and luster to the skin than the hand & nail cream of Comparative example 25 and Comparative example 26. That is, the results in Table 18 clearly show that the sodium salt of acylated peptide obtained by condensing non-hydroxyl lanolin fatty acid with a keratin-derived peptide is excellent in the effects of giving skin smoothness, moistness and luster, and is superior, in the effects, to the sodium salt of acylated peptide obtained in Comparative example 2 by condensing a lanolin fatty acid with a keratin-derived peptide.

As described above, the cosmetic composition for hair containing the acylated peptide or a salt thereof according to the present invention obtained by condensing a non-hydroxyl lanolin fatty acid with a protein-derived peptide, a hydrolysate of a protein, gives a hair with a moist feel and gloss and the like. In particular, it significantly inhibits damage of hair due to chemical treatment such as treatment for permanent wave. Further, the cosmetic composition for skin containing the acylated peptide or a salt thereof according to the present invention obtained by condensing a non-hydroxyl lanolin fatty acid with a protein-derived peptide, a hydrolysate of a protein, exhibits protecting function and moistening function onto skin, and gives skin an excellent feeling on use, such as smoothness and moistness of skin.

What we claim is:

1. A cosmetic composition containing an acylated peptide or a salt thereof which is obtained by condensing a protein-derived peptide produced by hydrolysis of a protein, with a lanolin-derived non-hydroxyl fatty acid containing over 30% to 45% by weigh of iso-fatty acid of the following formula (I), 30–35% by weight of anteiso-fatty acid of the following formula (II), 10–30% by weight of normal fatty acid of the following formula (III):

$$CH_3CH(CH_3)-(CH_2)_n-COOH \ (n=6\sim27) \qquad (I)$$

$$CH_3CH_2-CH(CH_3)-(CH_2)_n-COOH \ (n=6\sim26) \qquad (II)$$

$$CH_3(CH_2)_n-COOH \ (n=8\sim28) \qquad (III)$$

and less than 10% by weight of hydroxyl fatty acid, the total amount of said iso-fatty acid and said anteiso-fatty acid being at least 60% by weight.

2. The cosmetic composition according to claim 1, wherein the average number of carbon atoms of the iso-fatty acid of formula (I), the anteiso-fatty acid of formula (II), the normal fatty acid of formula (III) in the non-hydroxyl lanolin fatty acid is 15 to 24.

3. The cosmetic composition according to claim 1, wherein the average number of carbon atoms of the iso-fatty acid of formula (I), the anteiso-fatty acid of formula (II), the normal fatty acid of formula (III) in the non-hydroxyl lanolin fatty acid is 17 to 22.

4. The cosmetic composition according to claim 1, wherein the content of the iso-fatty acid of formula (I) is over 30 to 45 by weight, the content of the anteiso-fatty acid of formula (II) is 35–45% by weight and the content of the normal fatty acid of formula (III) is 12–16% by weight.

5. The cosmetic composition according to claim 1, wherein the protein-derived peptide is a collagen-derived peptide, a keratin-derived peptide, a silk protein-derived peptide, a casein-derived peptide, a soybean protein-derived peptide and a wheat protein-derived peptide.

6. An acylated peptide or a salt thereof which is obtained by condensing a protein-derived peptide produced by hydrolysis of a protein, with a lanolin-derived non-hydroxyl fatty acid containing over 30% to 45% by weight of iso-fatty acid of the following formula (I), 30–50% by weight of anteiso-fatty acid of the following formula (II), 10–30% by weight of normal fatty acid of the following formula (III):

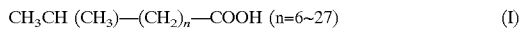

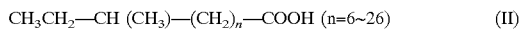

and less than 10% by weight of hydroxyl fatty acid, the total amount of said iso-fatty acid and said anteiso-fatty acid being at least 60% by weight.

7. The acylated peptide or salt thereof according to claim 6, wherein the lanolin-derived non-hydroxyl fatty acid contains 35–45% by weight of iso-fatty acid of formula (I).

8. The acylated peptide or a salt thereof according to claim 6, wherein the protein-derived peptide has a number average molecular weight of 100–30,000.

9. The acylated peptide or a salt thereof according to claim 8, wherein the protein-derived peptide has a number average molecular weight of 200–5,000.

10. A method of preparing an acylated peptide or a salt thereof, comprising:
   A) hydrolyzing a protein thereby producing a protein-derived peptide;
   B) condensing the protein-derived peptide with a lanolin-derived non-hydroxyl fatty acid containing over 30% to 45% by weight of iso-fatty acid of the following formula (I), 30–50% by weight of anteiso-fatty acid of the following formula (II), 10–30% by weight of normal fatty acid of the following formula (III):

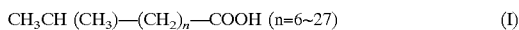

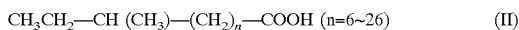

and less than 10% by weight of hydroxy fatty acid, the total amount of said iso-fatty acid and said anteiso-fatty acid being at least 60% by weight.

11. The method of preparing an acylated peptide or salt thereof according to claim 10, wherein the lanolin-derived non-hydroxyl fatty acid contains 35–45% by weight of iso-fatty acid of formula (I).

12. The method of preparing an acylated peptide or a salt thereof according to claim 10, wherein the condensing step comprises acylating the protein-derived peptide with a non-hydroxyl lanolin fatty acid halide in an aqueous solution in a pH range of 7–14.

13. The method of preparing an acylated peptide or a salt thereof according to claim 8, wherein the pH is controlled by adding alkali.

14. The method of preparing an acylated peptide or a salt thereof according to claim 13, wherein the alkali is sodium hydroxide or potassium hydroxide.

15. The method of preparing an acylated peptide or a salt thereof according to claim 12, wherein the non-hydroxyl lanolin fatty acid halide is a non-hydroxyl lanolin fatty acid chloride.

16. The method of preparing an acylated peptide or a salt thereof according to claim 10, wherein the condensing step comprises contacting the protein-derived peptide with a non-hydroxyl lanolin fatty acid under dehydration conditions.

17. The method of preparing an acylated peptide or a salt thereof according to claim 10, wherein the condensing step comprises contacting the protein-derived peptide with a lower alcohol ester of a non-hydroxyl lanolin fatty acid under dealcoholization conditions.

* * * * *